United States Patent [19]

Rogers et al.

[11] 4,383,851

[45] May 17, 1983

[54] 2-AMINO-6-FLUORONICOTINIC ACIDS AND DERIVATIVES THEREOF AND METHODS OF HERBICIDAL USE

[75] Inventors: Richard B. Rogers, Concord, Calif.; Jon S. Claus, Hanover, Va.; Eric A. Egli, Walnut Creek, Calif.

[73] Assignee: The Dow Chemical Company, Midland, Mich.

[21] Appl. No.: 289,432

[22] Filed: Aug. 3, 1981

[51] Int. Cl.$^3$ .................... A01N 43/40; C07D 213/55
[52] U.S. Cl. ........................................ 71/94; 546/318; 546/322
[58] Field of Search ..................... 546/318, 322; 71/94

[56] References Cited

U.S. PATENT DOCUMENTS 2,516,830  7/1950  Roe ..................................... 546/318
4,025,333  5/1977  Gulbenk ................................. 71/94

OTHER PUBLICATIONS

Renshaw et al., Chem. Abstracts, vol. 34, No. 17, pp.-6020, Sep. 10, 1940.
Bradlow et al., Journal of Organic Chem., vol. 14, pp.-509-515 (1949).
Roe et al., Journal of American Chem. Soc., vol. 71, pp.-4152-4153, (1949).
Beaty et al., Journal of the Chem. Soc., London, pp.-35-12-3515, (1951).
Hughes, Chem. Abstracts, vol. 48, No 18, pp.-1083-5g-10836a Sep. 25, 1954.
Ariens et al., Chem. Abstracts, vol. 49, No 13, pp.-908-8h-i, Jul. 10, 1955.
Streightoff, Chem. Abstracts, vol. 58, No. 5, pp.-48-36a-b, Mar. 4, 1968.

Primary Examiner—Alan L. Rotman

[57] ABSTRACT

Novel 2-amino-6-fluoronicotinic acids, amides and esters, herbicidal compositions containing these compounds and methods of using such compounds for the control of wild oats in wheat.

21 Claims, No Drawings

2-AMINO-6-FLUORONICOTINIC ACIDS AND DERIVATIVES THEREOF AND METHODS OF HERBICIDAL USE

BACKGROUND OF THE INVENTION

1. Field of the Invention

This invention relates (a) to novel 2-amino-6-fluoronicotinic acids, amides and esters thereof, (b) to herbicidal compositions of such novel compounds and (c) to preemergent and postemergent methods of using such compounds for the control of grassy weeds in non-crop areas as well as in the presence of many valuable crops.

2. Description of the Prior Art

U.S. Pat. No. 2,516,830 issued July 25, 1950 discloses various nicotinic acid compounds such as 5-fluoronicotinic acid and 5-fluoronicotinamide and their use as antimetabolites against streptococci.

Chemical Abstracts 43:9069b discloses the synthesis of certain alpha-halogenated pyridine compounds, including 6-fluoronicotinamide and Chemical Abstracts 58:4836a discloses the inhibition of bacteria by 5-fluoronicotinic acid.

SUMMARY OF THE INVENTION

The present invention is directed to novel 2-amino-6-fluoronicotinic acids, amides and esters having the formula

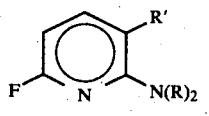

wherein R represents hydrogen or methyl; R' represents CN or

wherein X represents SAr, OR", $NH_2$ or OM; Ar represents

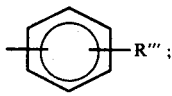

R" represents H, $C_1$–$C_4$ alkyl,

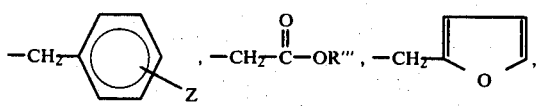

alkenyl, alkynyl, hydroxyalkyl, aminoalkyl or alkoxyalkyl; R''' represents H or $C_1$–$C_4$ alkyl; M represents alkali metal, ammonia, alkanol amine, or mono or dialkylamine and Z represents hydrogen, Cl, Br, F, $CH_3$, $OCH_3$ or $CF_3$.

Preferred compounds are 2-amino-6-fluoronicotinic acid, ethyl 2-amino-6-fluoro-3-pyridinecarboxylate, benzyl 2-amino-6-fluoro-3-pyridinecarboxylate, β-methoxyethyl 2-amino-6-fluoro-3-pyridinecarboxylate, and 3-fluorobenzyl 2-amino-6-fluoro-3-pyridinecarboxylate.

The foregoing compounds, preferably formulated as liquid compositions, are used according to the methods of the invention for the control of undesired vegetation, particularly grassy weeds, and most particularly wild oats, advantageously in the presence of many valuable crops. Some of the compounds are more useful in postemergent applications while the others are useful in preemergent operations as well.

The compounds of the above formula, hereinafter referred to for convenience as "active ingredients", have been found to be especially active as herbicides for the control of undesired vegetation, for example, grassy or graminaceous weeds. Accordingly, the present invention also encompasses compositions containing one or more active ingredients as well as preemergent and postemergent methods of controlling undesired plant growth, especially in the presence of valuable crops, particularly wheat and broadleaf crops. Such methods comprise applying a herbicidally-effective amount of one or more active ingredients to the locus of the undesired plants, that is, the seeds, foliage, stems and roots or other parts of the growing plants or soil in which the plants are growing or may be found.

DETAILED DESCRIPTION OF THE INVENTION

The term "herbicide" is used herein to mean an active ingredient which controls or adversely modifies the growth of plants because of phytotoxic or other effects substantial enough to seriously retard the growth of the plant or to further damage the plant sufficiently to kill it.

By "growth controlling" or "herbicidally-effective" amount is meant an amount of active ingredient which causes a modifying effect and includes deviations from natural development, killing, regulation, desiccation, retardation, and the like.

The term "plants" is meant to include germinant seeds, emerging seedlings, and established vegetation.

The term "$C_1$–$C_4$ alkyl, alkenyl or alkynyl" refers to groups which may be straight or branched chain and contain from 1 to 4 carbon atoms. The terms "alkoxyalkyl, hydroxyalkyl and aminoalkyl" refer to groups having from 1 to 4 carbon atoms in the alkyl and/or alkoxy portion of the molecule.

The active ingredients of the present invention are generally oils or crystalline solids at ambient temperatures.

The compounds of the present invention may be prepared from the appropriate ester of 2,6-difluoropyridine-3-carboxylic acid by adding the ester to a vigorously stirred solution of anhydrous ammonia ($\geq 3$ equivalents) in formamide. Stirring is continued at room temperature until thin layer chromatography (silica gel, 7:3 hexane-acetone or silica gel, 9:1 chloroform-methanol) indicates the absence of the starting difluoro compound (30 minutes—16 hours). During this period the starting difluoro compound dissolves and then usually a solid separates from the solution. When the reaction is complete, the mixture is poured into water (1–2 liters) whereupon a solid usually separates. This may be extracted with a suitable solvent, such as ethyl acetate, chloroform, or ether (this is necessary if no solid separates) or filtered and air dried. If the material is extracted with a solvent, the organic phase is dried ($MgSO_4$) and the solvent evaporated. In all cases the material obtained from the reaction is a mixture of the desired 2-amino-6-fluoropyridine-3-carboxylic acid ester and its isomer 6-amino-2-fluoropyridine-3-carboxylic acid ester. Separation of these two isomers may be effected in one of two ways: (1) The mixture is subjected to continuous extraction via a Soxhlet apparatus using either hexane or methyl cyclohexane as the solvent. This extracts the desired 2-amino-6-fluoro isomer leaving the isomeric 6-amino-2-fluoropyridine-3-carboxylic acid ester as an undissolved solid. Recrystallization from appropriate solvents completes the purification process. (2) The mixture may be separated via preparative high pressure liquid chromatography on silica gel using an appropriate combination of acetone in hexane as an eluent (5–30% acetone in hexane). The desired 2-amino-6-fluoropyridine-3-carboxylic acid ester always elutes first from the column. Recrystallization from an appropriate solvent completes the purification process.

EXAMPLE 1

2-Amino-6-fluoropyridine-3-carboxylic acid, n-butyl ester

To a mechanically stirred solution of ammonia (14 grams (g)) in formamide (300 milliliter (ml)) was added all at once butyl 2,6-difluoropyridine-3-carboxylate (29 g, 0.135 mole). The resulting mixture was stirred overnight at room temperature. The mixture was then poured into water (1500 ml) and the product was filtered. After washing with several portions of water, the solid was dissolved in chloroform, dried (MgSO$_4$) and the solvent evaporated. The resulting solid (26 g, m.p.=84°–120° C.) was separated via preparative high pressure liquid chromatography (8:2 hexane-acetone) to give first the desired butyl 2-amino-6-fluoropyridine-3-carboxylate (10 g) which after recrystallization from hexane had a m.p.=88.5°–90.5° C. Eluting second was the isomeric butyl 6-amino-2-fluoropyridine-3-carboxylate (9 g) which after recrystallization from toluene had a m.p.=132.5°–134° C.

EXAMPLE 2

2-Amino-6-fluoropyridine-3-carboxylic acid, benzyl ester

To a stirred solution of ammonia (15 g) in formamide (250 ml) was added all at once benzyl 2,6-difluoropyridine-3-carboxylate (20 g, 0.08 mole). The mixture slowly became homogeneous, then a solid began to separate. After two hours, the mixture was poured into water (1000 ml) and the solid filtered. The solid was washed with several portions of water then air dried. Continuous extraction for one hour via a Soxhlet extraction apparatus using hexane as the solvent gave, after concentrating to 250 ml and cooling, 6.0 g (30%) of the desired benzyl 2-amino-6-fluoropyridine-3-carboxylate: m.p.=92°–94° C. The hexane insoluble material was recrystallized from a small volume of acetone to give 5.5 g (28%) of the isomeric benzyl 6-amino-2-fluoropyridine-3-carboxylate: m.p.=157.5°–159.5° C.

EXAMPLE 3

2-Amino-6-fluoropyridine-3-carboxylic acid

A solution of benzyl 2-amino-6-fluoropyridine-3-carboxylate (2.0 g, 0.008 mole) in ethanol (250 ml) containing 5 percent Palladium on charcoal was shaken in a hydrogen atmosphere (50 psi was the initial pressure) using a Paar apparatus. Hydrogen uptake ceased after 10–15 minutes. After purging the hydrogen from the system, the catalyst was removed by filtration, and the solvent evaporated to give 1.2 g (94 percent) of the desired acid. Recrystallization from water gave an analytical sample: m.p.=205–214 decompose.

Employing the above procedures, the following compounds were prepared:

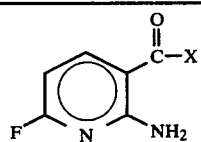

| X | M.P. °C. | | Analysis | | |
|---|---|---|---|---|---|
| | | | C | H | N |
| Nitrile $\begin{bmatrix} \text{O} \\ \| \\ \text{CX} = -\text{C}\equiv\text{N} \end{bmatrix}$ | 155–158 | Theory | 52.56 | 2.94 | 30.65 |
| | | Found | 52.65 | 2.96 | 30.24 |
| —NH$_2$ | 198–200 | Theory | 46.45 | 3.90 | 27.09 |
| | | Found | 46.37 | 3.74 | 27.09 |
| —OCH$_2$CH$_3$ | 127–128 | Theory | 52.19 | 4.89 | 15.21 |
| | | Found | 52.16 | 5.01 | 15.05 |
| —OCH$_2$CH$_2$CH$_2$CH$_3$ | 88.5–90.5 | Theory | 56.59 | 6.17 | 13.20 |
| | | Found | 56.67 | 6.19 | 13.17 |
| —OH | 205–214 dec. | Theory | 46.16 | 3.23 | 17.95 |
| | | Found | 46.18 | 3.41 | 17.67 |
| —OCH$_2$Ph | 92–94 | Theory | 63.41 | 4.50 | 11.38 |
| | | Found | 63.20 | 4.42 | 11.41 |
| —OCH$_2$CH$_3$ [NH$_2$ = N(CH$_3$)$_2$] | R.I. 1.5260 | Theory | 56.59 | 6.17 | 13.20 |
| | | Found | 56.51 | 6.67 | 13.21 |
| —OCH$_2$CH$_3$ [NH$_2$ = NHCH$_3$] | 62.5–65 | Theory | 54.54 | 5.60 | 14.14 |
| | | Found | 54.09 | 5.60 | 13.94 |
| —O—CH(CH$_3$)$_2$ | 88–90 | Theory | 54.54 | 5.60 | 14.14 |
| | | Found | 54.43 | 5.57 | 14.08 |
| —OCH$_3$ | 128–131 | Theory | 49.41 | 4.15 | 16.47 |
| | | Found | 49.06 | 4.14 | 16.13 |

-continued

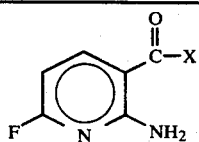

| X | M.P. °C. | Analysis | | | |
|---|---|---|---|---|---|
| | | | C | H | N |
| —OCH₂—⟨⟩—Cl | 141–145 | Theory | 55.62 | 3.59 | 9.98 |
| | | Found | 55.63 | 3.61 | 9.98 |
| —OCH₂—⟨⟩—CH₃ | 122–123.5 | Theory | 64.60 | 5.03 | 10.77 |
| | | Found | 64.28 | 4.93 | 10.66 |
| —OCH₂—⟨⟩—OCH₃ | 139–141 | Theory | 60.86 | 4.74 | 10.14 |
| | | Found | 60.98 | 4.82 | 10.08 |
| —OCH₂CH₂OCH₃ | 73–76 | Theory | 50.46 | 5.18 | 13.08 |
| | | Found | 50.44 | 5.17 | 13.26 |
| —OCH₂—⟨⟩—F | 129–131 | Theory | 59.09 | 3.81 | 10.60 |
| | | Found | 58.85 | 3.82 | 10.56 |
| —OCH₂C≡CH | 128–130 | Theory | 55.67 | 3.63 | 14.43 |
| | | Found | 55.52 | 3.77 | 14.59 |
| —OCH₂CH=CH₂ | 71–73 | Theory | 55.10 | 4.62 | 14.28 |
| | | Found | 54.92 | 4.73 | 14.53 |
| —OCH₂—⟨⟩ (o-Cl) | 122–124.5 | Theory | 55.62 | 3.59 | 9.98 |
| | | Found | 55.29 | 3.58 | 9.98 |
| —OCH₂—⟨⟩ (o-F) | 111–113 | Theory | 59.09 | 3.81 | 10.60 |
| | | Found | 58.61 | 3.88 | 10.51 |
| —OCH₂—⟨⟩ (Cl) | 115–117.5 | Structure confirmed by NMR | | | |
| —OCH₂—⟨⟩ (CF₃) | 123.5–126 | Theory | 53.51 | 3.21 | 8.92 |
| | | Found | 53.29 | 3.28 | 8.87 |
| —OCH₂CH₂N(CH₃)₂ | 35–41 | Structure confirmed by NMR | | | |
| —OCH₂CH₂OCH₂Ph | 64–65.5 | Theory | 62.06 | 5.21 | 9.65 |
| | | Found | 61.90 | 5.13 | 9.72 |
| —OCH₂CH₂OH | 116–119 | Theory | 48.00 | 4.53 | 14.00 |
| | | Found | 47.95 | 4.49 | 13.89 |
| —OCH₂-furyl | 88–96 | Theory | 55.93 | 3.84 | 11.86 |
| | | Found | 56.19 | 3.98 | 11.47 |
| —S—⟨⟩—C(CH₃)₃ | 153.5–155.5 | Theory | 63.13 | 5.63 | 9.20 |
| | | Found | 63.54 | 5.91 | 9.09 |
| —OCH₂COCH₂CH₃ | 106–107.5 | Theory | 49.59 | 4.58 | 11.57 |
| | | Found | 49.61 | 4.58 | 11.62 |

The compounds of the present invention have been found to be particularly suitable for use in methods for the pre and postemergent control of grassy weeds. The active ingredients of the present invention have been found to have advantage over prior art compounds in the control of wild oats. In addition, the present compounds are sufficiently tolerant towards most broad leafed crops and grassy crops, such as wheat, to contemplate control of grassy weeds therein at substantially commercially practicable levels, particularly so with the preferred compounds.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid or solid compositions comprising one or more of the active ingredients, can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

The active ingredients can also be applied as aerosols, e.g., by dispersing them by means of a compressed gas such as one of the hydrocarbon successors to the fluorocarbons.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products, e.g., Pluronic 61 (molecular weight about 1000), polyethylene glycol ester of tall oil acids, sodium octophenoxyethoxyethyl sulfate, tris(polyoxyethylene)sorbitan monostearate (Tween 60), and sodium dihexylsulfosuccinate.

The concentration of the active ingredients in solid or liquid compositions generally is from about 0.003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15-50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power dusters, boom and hand sprayers, spray dusters, by addition to irrigation water, and by other conventional means. The compositions can also be applied from airplanes as a dust or spray since the active ingredients are effective at very low application rates.

The active ingredients of the present invention have been found to possess desirable herbicidal activity in general against grassy weeds such as foxtail, barnyard grass, wild oats and crabgrass in preemergent operations and also against the same grasses in postemergent operations. The active ingredients of the present invention have been found to possess particularly desirable herbicidal activity against wild oats in postemergent operations with selectivity to wheat and broadleaf crops.

The exact rate to be applied is dependent not only on a specific active ingredient being applied, but also on a particular action desired (e.g., general or selective control), the plant species to be modified and the stage of growth thereof as well as the part of the plant to be contacted with the toxic active ingredient. Thus, it is to be understood that all of the active ingredients of the present invention and compositions containing the same may not be equally effective at similar concentrations or against the same plant species. In non-selective pre-emergence and foliar treatments, the active ingredients of the invention are usually applied at an approximate rate of from about 0.5 to about 10 pounds/acre, but lower or higher rates may be appropriate in some cases, such as 0.10 to about 20 pounds/acre or more. In preemergent operations for selective uses, a dosage of about 0.10 to about 20 pounds/acre or more is generally applicable, a rate of 0.25 to 10 pounds/acre being preferred and about 0.5 to about 5 pounds/acre being most preferred.

In postemergent operations a dosage of about 0.10 to about 20 pounds/acre or more is generally applicable, although not all compounds are equally effective and some weeds are more difficult to control. A dosage rate in the range of about 0.25 to about 5.0 pounds/acre is preferred in selective postemergent control of annual grassy weeds.

In view of the foregoing and the following disclosures, one skilled in the art can readily determine the optimum rate to be applied in any particular case.

In representative operations, each compound to be utilized in a series of tests is dissolved in acetone to one half of the final volume (twice the final concentration) to be used and the acetone solution in each case is admixed with an equal volume of water containing 0.1 percent by weight of Tween-20 surface active material (Tween-20 is a trademark of Atlas Chemical Company). Each compound is selected from a group consisting of compounds according to the invention. The compositions, generally in the nature of an emulsion, were employed to treat separate respective seed beds of sandy loam soil of good nutrient content wherein each seed bed contained separate groups of good viable seeds, each group being of one of a predetermined plant species. The various beds were positioned side by side and exposed to substantially identical conditions of temperature and light. Each bed was maintained so as to prevent any interaction with test compounds in different seed beds. Each seed bed was treated with one of the compositions as a soil drench applied at predetermined rates to deposit a predetermined amount of a given test compound uniformly throughout the surface of the bed. The compositions were applied to the seed beds so that different seed beds of a given plant species were treated with one of each of the test compounds. Another seed bed was treated only with water to serve as a control. After treatment, the seed beds were maintained for two weeks under greenhouse conditions conducive for good plant growth and watered as necessary. The specific plant species, test compound and dosage and the percent preemergent control obtained are set forth in Table I below. Control refers to the reduction in growth compared to the observed results of the same species.

TABLE I

PREEMERGENCE CONTROL OF PLANT SPECIES

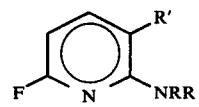

| Compound Tested | | | Dosage in Pounds/Acre | % Control | | | | | | |
|---|---|---|---|---|---|---|---|---|---|---|
| R | R' | X | | Rice | Wheat | Barnyard Grass | Crab-Grass | Foxtail | Johnson Grass | Wild-Oats |
| H$_2$ | O<br>‖<br>−C−X | −OCH$_2$−◯ | 4 | 90 | 90 | 90 | 90 | 80 | 95 | 98 |
| | | | 2 | 90 | 20 | 95 | 70 | 30 | 40 | 95 |
| | | | 1 | 30 | 0 | 30 | 30 | 0 | 20 | 80 |
| | | | 0.5 | 0 | 0 | 0 | 0 | 0 | 0 | 60 |
| | | | 0.25 | 0 | 0 | 0 | 0 | 0 | 0 | 0 |
| H$_2$ | O<br>‖<br>−C−X | −OH | 4 | 100 | 90 | 98 | 100 | 30 | 70 | 100 |
| | | | 2 | 100 | 100 | 70 | 100 | 40 | 70 | 98 |
| | | | 1 | 30 | 40 | 60 | 0 | 0 | 50 | 40 |
| | | | 0.5 | 0 | 0 | 50 | 0 | 0 | 0 | 30 |
| | | | 0.25 | 0 | 0 | 0 | 0 | 0 | 0 | 0 |
| H$_2$ | O<br>‖<br>−C−X | −OCH$_2$−◯−F | 4 | 0 | 0 | 70 | 30 | 0 | 90 | 80 |
| | | | 2 | 0 | 0 | 0 | 0 | 0 | 60 | 90 |
| | | | 1 | 0 | 0 | 0 | 0 | 0 | 0 | 40 |
| | | | 0.5 | 0 | 0 | 0 | 0 | 0 | 0 | 30 |
| | | | 0.25 | 0 | 0 | 0 | 0 | 0 | 0 | 0 |
| H$_2$ | O<br>‖<br>−C−X | H<br>\|<br>−OC−CH$_3$<br>\|<br>CH$_3$ | 4 | 0 | 30 | 0 | 0 | 0 | 0 | 30 |
| | | | 2 | 0 | 0 | 0 | 0 | 0 | 0 | 0 |
| | | | 1 | 0 | 0 | 0 | 0 | 0 | 0 | 0 |
| | | | 0.5 | 0 | 0 | 0 | 0 | 0 | 0 | 0 |
| | | | 0.25 | 0 | 0 | 0 | 0 | 0 | 0 | 0 |
| HCH$_3$ | O<br>‖<br>−C−X | −OCH$_2$CH$_3$ | 4 | 0 | 0 | 0 | 0 | 0 | 0 | 100 |
| | | | 2 | 0 | 0 | 0 | 0 | 0 | 0 | 0 |
| | | | 1 | 0 | 0 | 0 | 0 | 0 | 0 | 0 |
| | | | 0.5 | 0 | 0 | 0 | 0 | 0 | 0 | 0 |
| | | | 0.25 | 0 | 0 | 0 | 0 | 0 | 0 | 0 |
| H$_2$ | O<br>‖<br>−C−X | −OCH$_2$CH$_2$OCH$_3$ | 4 | 100 | 80 | 100 | 100 | 20 | 30 | 95 |
| | | | 2 | 100 | 20 | 98 | 80 | 0 | 20 | 95 |
| | | | 1 | 0 | 0 | 30 | 20 | 0 | 0 | 60 |
| | | | 0.5 | 0 | 0 | 0 | 0 | 0 | 0 | 30 |
| | | | 0.25 | 0 | 0 | 0 | 0 | 0 | 0 | 0 |
| H$_2$ | O<br>‖<br>−C−X | −OCH$_2$−◯−F | 4 | 90 | 0 | 90 | 40 | 0 | 50 | 98 |
| | | | 2 | 70 | 0 | 70 | 0 | 0 | 0 | 95 |
| | | | 1 | 20 | 0 | 30 | 0 | 0 | 0 | 80 |
| | | | 0.5 | 0 | 0 | 0 | 0 | 0 | 0 | 50 |
| | | | 0.25 | 0 | 0 | 0 | 0 | 0 | 0 | 0 |

On repeating the foregoing test procedures using other substituted 2-amino-6-fluoronicotinic acids of the invention and derivatives herein embraced substantially the same preemergent herbicidal results are obtained.

So as to illustrate clearly the phytotoxic properties of the various active ingredients of the present invention applied postemergently, a group of controlled greenhouse experiments is described below.

Various species of plants were planted in beds of good agricultural soil in a greenhouse. After the plants had emerged and grown to a height of about 2-6 inches a portion of the plants were sprayed with an aqueous mixture, made by mixing a selected active ingredient and emulsifier or dispersant with about 1:1 water-acetone, employing sufficient amounts of the treating composition to provide application rates of 4000 parts per million (ppm) or about 10 pounds per acre and in some cases at lower rates. Other plants were left untreated to serve as controls.

After a period of 2-3 weeks, the effect of the respective test ingredients used on respective groups of plants was evaluated by a comparison with the control groups of the plants. The results are tabulated below in Table II.

percent control of wild oats; p-methoxybenzyl 2-amino-6-fluoro-3-pyridinecarboxylate gave 20 percent control of wheat and barnyard grass, 30 percent control of crabgrass, 70 percent control of Johnson grass and 90 percent control of wild oats; propargyl 2-amino-6-fluoro-3-pyridinecarboxylate gave 100 percent control of wild oats with no control of the other plant species and 2-amino-6-fluoro nicotinamide, at 500 ppm, gave 100 percent control of crabgrass with no control of the other plant species.

What is claimed is:

1. A compound having the formula

TABLE II
POSTEMERGENCE CONTROL OF PLANT SPECIES

| Compound Tested | | | | % Control | | | | | | |
|---|---|---|---|---|---|---|---|---|---|---|
| R | R' | X | | Dosage (PPM) | Rice | Wheat | Barnyard Grass | Crab-grass | Foxtail | Johnson Grass | Wild-Oats |
| H₂ | $-\overset{O}{\underset{\|}{C}}-X$ | $-OCH_2-\phi$ | | 2000 | 50 | 100 | 100 | 100 | 0 | 30 | 100 |
| | | | | 1000 | 0 | 98 | 100 | 100 | 0 | 0 | 100 |
| | | | | 500 | 0 | 90 | 80 | 100 | 0 | 0 | 100 |
| | | | | 250 | 0 | 70 | 40 | 40 | 0 | 0 | 97 |
| | | | | 125 | 0 | 40 | 20 | 30 | 0 | 0 | 95 |
| | | | | 62.5 | 0 | 0 | 0 | 0 | 0 | 0 | 30 |
| H₂ | $-\overset{O}{\underset{\|}{C}}-X$ | —OH | | 2000 | 80 | 90 | 100 | 100 | 80 | 98 | 100 |
| | | | | 1000 | 70 | 80 | 100 | 100 | 30 | 40 | 100 |
| | | | | 500 | 30 | 95 | 100 | 95 | 20 | 30 | 100 |
| | | | | 250 | 0 | 80 | 98 | 40 | 0 | 0 | 95 |
| | | | | 125 | 0 | 70 | 20 | 30 | 0 | 0 | 97 |
| | | | | 62.5 | 0 | 40 | 0 | 0 | 0 | 0 | 50 |
| H₂ | $-\overset{O}{\underset{\|}{C}}-X$ | $-OCH_2-\phi(F)$ | | 2000 | 30 | 0 | 100 | 100 | 30 | 0 | 98 |
| | | | | 1000 | 0 | 0 | 80 | 100 | 0 | 0 | 95 |
| | | | | 500 | 0 | 0 | 30 | 20 | 0 | 0 | 90 |
| | | | | 250 | 0 | 0 | 0 | 0 | 0 | 0 | 90 |
| | | | | 125 | 0 | 0 | 0 | 0 | 0 | 0 | 90 |
| | | | | 62.5 | 0 | 0 | 0 | 0 | 0 | 0 | 70 |

In postemergent operations carried out as described above, ethyl 2-amino-6-fluoro-3-pyridinecarboxylate gave 20 percent control of foxtail and Johnson grass and 95 percent control of wild oats at 500 ppm. There was no control of rice, wheat, barnyard grass or crabgrass. Similarly, at 2000 ppm, p-fluorobenzyl 2-amino-6-fluoro-3-pyridinecarboxylate gave 30 percent control of rice, 20 percent control of crabgrass and 60 percent control of wild oats with no control of wheat, barnyard grass, foxtail or Johnson grass while the corresponding p-chlorobenzyl compound gave 10 percent control of rice, 20 percent control of wheat and 90 percent control of wild oats. At 1000 ppm isopropyl 2-amino-6-fluoro-3-pyridine carboxylate gave 30 percent control of barnyard grass and 95 percent control of wild oats with no control of the other plant species above; ethyl-2-methylamino-6-fluoro-3-pyridinecarboxylate gave 20 percent control of rice and 80 percent control of wild oats and methyl 2-amino-6-fluoro-3-pyridinecarboxylate gave 20 percent control of barnyard grass and 100 percent control of wild oats.

In further postemergent operations p-methylbenzyl-2-amino-6-fluoro-3-pyridinecarboxylate, at 2000 ppm, gave 20 percent control of barnyard grass and Johnson grass, 30 percent control of wheat and crabgrass and 95

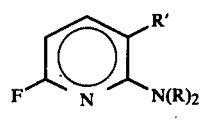

wherein R represents hydrogen or methyl; R' represents

wherein X represents OR", or OM;
R" represents H, C₁-C₄ alkyl, alkoxyalkyl or

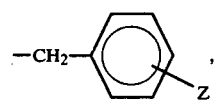

M represents alkali metal, ammonia, alkanol amine, or mono or dialkylamine and Z represents hydrogen, Cl, Br, F, CH₃, OCH₃ or CF₃ wherein each alkyl, alkoxy or alkanol group contains 1-4 carbon atoms.

2. Compound of claim 1 wherein R is hydrogen and R' is

wherein X is OH, ethoxy or OR" wherein R" is benzyl.

3. Compound of claim 2 which is 2-amino-6-fluoronicotinic acid.

4. Compound of claim 2 which is ethyl 2-amino-6-fluoro-3-pyridinecarboxylate.

5. Compound of claim 2 which is benzyl 2-amino-6-fluoro-3-pyridinecarboxylate.

6. Compound of claim 1 which is 3-fluorobenzyl 2-amino-6-fluoro-3-pyridinecarboxylate.

7. Compound of claim 1 which is beta-methoxyethyl 2-amino-6-fluoro-3-pyridinecarboxylate.

8. An herbicidal composition comprising an inert carrier and an herbicidally effective amount of a compound having the formula

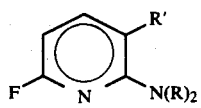

wherein R represents hydrogen or methyl; R' represents

wherein X represents OR", or OM;
R" represents H, $C_1$–$C_4$ alkyl, alkoxyalkyl or

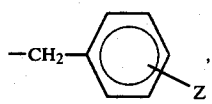

M represents alkali metal, ammonia, alkanol amine, or mono or dialkylamine and Z represents hydrogen, Cl, Br, F, $CH_3$, $OCH_3$ or $CF_3$ wherein each alkyl, alkoxy, or alkanol group contains 1–4 carbon atoms.

9. Composition of claim 8 wherein the compound is 2-amino-6-fluoronicotinic acid.

10. Composition of claim 8 wherein the compound is ethyl 2-amino-6-fluoro-3-pyridinecarboxylate.

11. Composition of claim 8 wherein the compound is benzyl 2-amino-6-fluoro-3-pyridinecarboxylate.

12. Composition of claim 8 wherein the compound is 3-fluorobenzyl 2-amino-6-fluoro-3-pyridine carboxylate.

13. Composition of claim 8 wherein the compound is β-methoxyethyl 2-amino-6-fluoro-3-pyridinecarboxylate.

14. Method for selectively controlling wild oats in grassy crops such as wheat which comprises applying to said grassy crops, or to the soil in which said grassy crops are to be grown, an herbicidally effective amount of a compound having the formula

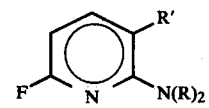

wherein R represents hydrogen or methyl; R' represents

wherein X represents OR", or OM;
R" represents H, $C_1$–$C_4$ alkyl, alkoxyalkyl or

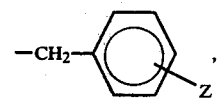

M represents alkali metal, ammonia, alkanol amine, or mono or dialkylamine and Z represents hydrogen, Cl, Br, F, $CH_3$, $OCH_3$ or $CF_3$ wherein each alkyl, alkoxy or alkanol group contains 1–4 carbon atoms.

15. Method of claim 14 wherein the compound is 2-amino-6-fluoronicotinic acid.

16. Method of claim 14 wherein the compound is ethyl 2-amino-6-fluoro-3-pyridinecarboxylate.

17. Method of claim 14 wherein the compound is benzyl 2-amino-6-fluoro-3-pyridinecarboxylate.

18. Method of claim 14 wherein the compound is 3-fluorobenzyl 2-amino-6-fluoro-3-pyridinecarboxylate.

19. Method of claim 14 wherein the compound is β-methoxyethyl 2-amino-6-fluoro-3-pyridinecarboxylate.

20. Method of claim 14 wherein the compound is applied preemergently at a rate of 0.10 to 20 pounds/acre.

21. Method of claim 14 wherein the compound is applied postemergently at a rate of 0.10 to 20 pounds/acre.

* * * * *